(12) United States Patent
Lee et al.

(10) Patent No.: US 11,484,621 B2
(45) Date of Patent: Nov. 1, 2022

(54) CATALYST STRUCTURE FOR OZONE DECOMPOSITION

(71) Applicant: Purespace Inc., Busan (KR)

(72) Inventors: Sun Young Lee, Seoul (KR); Jae Sung Lee, Seoul (KR)

(73) Assignee: Purespace Inc., Busan (KR)

( * ) Notice: Subject to any disclaimer, the term of this patent is extended or adjusted under 35 U.S.C. 154(b) by 355 days.

(21) Appl. No.: 16/638,805

(22) PCT Filed: Jun. 21, 2019

(86) PCT No.: PCT/KR2019/007523
§ 371 (c)(1),
(2) Date: Feb. 13, 2020

(87) PCT Pub. No.: WO2020/036303
PCT Pub. Date: Feb. 20, 2020

(65) Prior Publication Data
US 2021/0213155 A1    Jul. 15, 2021

(30) Foreign Application Priority Data
Aug. 14, 2018 (KR) .................. 10-2018-0095103

(51) Int. Cl.
| | | |
|---|---|---|
| *A61L 9/20* | (2006.01) | |
| *B01D 53/00* | (2006.01) | |
| *B01D 53/86* | (2006.01) | |
| *B01D 53/88* | (2006.01) | |
| *B01J 21/06* | (2006.01) | |
| *B01J 21/14* | (2006.01) | |
| *B01J 23/34* | (2006.01) | |
| *B01J 35/00* | (2006.01) | |
| *B01J 35/02* | (2006.01) | |

(52) U.S. Cl.
CPC ............ *A61L 9/205* (2013.01); *B01D 53/007* (2013.01); *B01D 53/864* (2013.01); *B01D 53/8634* (2013.01); *B01D 53/8668* (2013.01); *B01D 53/8675* (2013.01); *B01D 53/885* (2013.01); *B01J 21/063* (2013.01); *B01J 21/14* (2013.01); *B01J 23/34* (2013.01); *B01J 35/004* (2013.01); *B01J 35/023* (2013.01); *A61L 2209/11* (2013.01); *B01D 2255/2073* (2013.01); *B01D 2255/20707* (2013.01); *B01D 2255/802* (2013.01); *B01D 2255/9202* (2013.01); *B01D 2257/106* (2013.01); *B01D 2257/406* (2013.01); *B01D 2257/708* (2013.01); *B01D 2257/7022* (2013.01); *B01D 2257/91* (2013.01); *B01D 2259/804* (2013.01)

(58) Field of Classification Search
CPC ........ B01D 53/864; B01D 2255/20707; B01D 2259/804; B01D 2257/7022; B01D 53/8668; B01D 2257/708; B01D 2258/06; B01D 2255/802; B01D 2257/406; B01D 53/885; B01D 53/8675; B01D 53/007; B01D 2255/9202; B01D 53/8634; B01D 2257/91; B01J 21/063; B01J 35/004; B01J 35/04; B01J 21/14; B01J 35/023; B01J 23/34; A61L 2209/212; A61L 2209/11; A61L 9/205; A61L 2202/13
See application file for complete search history.

(56) References Cited

U.S. PATENT DOCUMENTS

| | | | |
|---|---|---|---|
| 2004/0040831 A1 | 3/2004 | Hong et al. | |
| 2006/0204656 A1* | 9/2006 | Thompson | ............... B05D 3/02 427/430.1 |
| 2018/0264160 A1* | 9/2018 | Benedek | ................... A61L 2/10 |
| 2019/0240371 A1* | 8/2019 | Benedek | ................ B01D 46/80 |
| 2022/0133942 A1* | 5/2022 | Benedek | ................. A61L 9/205 422/121 |

FOREIGN PATENT DOCUMENTS

| | | | | |
|---|---|---|---|---|
| CN | 1174519 A | 2/1998 | | |
| CN | 101406831 A | 4/2009 | | |
| CN | 101797475 A | 8/2010 | | |
| CN | 106 237 841 A | * 12/2016 | ......... | B01D 53/8668 |
| CN | 105 692 701 B | * 5/2018 | ............ | C01G 45/02 |
| EP | 0 931 581 A1 | 7/1999 | | |
| EP | 0 854 752 A1 | 8/2005 | | |
| JP | 11-076762 | 3/1999 | | |
| JP | 2002204653 | 7/2002 | | |
| JP | 2007224714 | 9/2007 | | |
| JP | 2009254961 | 11/2009 | | |
| JP | 2010-043808 | 2/2010 | | |
| JP | 2012 236 144 A | * 12/2012 | ............ | Y02A 50/20 |
| JP | 2001039764 | 2/2021 | | |
| JP | 2022 013 546 A | * 1/2022 | | |

(Continued)

OTHER PUBLICATIONS

Office Action for Japanese Patent Application No. 2020-510106, dated Mar. 9, 2021 (w/English translation).
International Search Report and Written Opinion for PCT/KR2019/007523 (dated Oct. 2, 2019).
Notice of Allowance for Korean Patent Application No. 10-2018-0095103 (dated Apr. 10, 2019) (with machine translation).
Office Action for Korean Patent Application No. 10-2018-0095103 (dated Dec. 11, 2019) (with machine translation).

(Continued)

*Primary Examiner* — Timothy C Vanoy
(74) *Attorney, Agent, or Firm* — Klarquist Sparkman, LLP

(57) ABSTRACT

Provided are a catalyst structure for ozone decomposition including a support containing a porous inorganic material, and an $\alpha$-$MnO_2$ catalyst located on at least a portion of inner pores and a surface of the support, an air-cleaning method using the same, and an air-cleaning device and an air-cleaning system each including the catalyst structure for ozone decomposition.

21 Claims, 9 Drawing Sheets

(56) References Cited

FOREIGN PATENT DOCUMENTS

| KR | 10-0460254 | 12/2004 | | |
|----|------------|---------|---|---|
| KR | 10-2018-0031185 | 3/2018 | | |
| WO | WO 96/22148 | 7/1996 | | |
| WO | WO 00/13790 A1 * | 3/2000 | ............. | B01J 23/34 |
| WO | WO 2015 126 982 A2 * | 8/2015 | ............. | B01J 19/12 |
| WO | WO2018/005052 | 1/2018 | | |

OTHER PUBLICATIONS

Extended Search Report from the European Patent Office dated Apr. 5, 2022, from European Patent Application No. 19845758.2 (9 pages).

Written Opinion from the Intellectual Property Office of Singapore dated Apr. 27, 2022, from Singapore Patent Application No. 11202000956Q (7 pages).

Chinese Office Action dated Jun. 20, 2022, from corresponding Chinese Application No. 201980003889.X (19 pages) (with attached English translation).

* cited by examiner

[Figure 1]
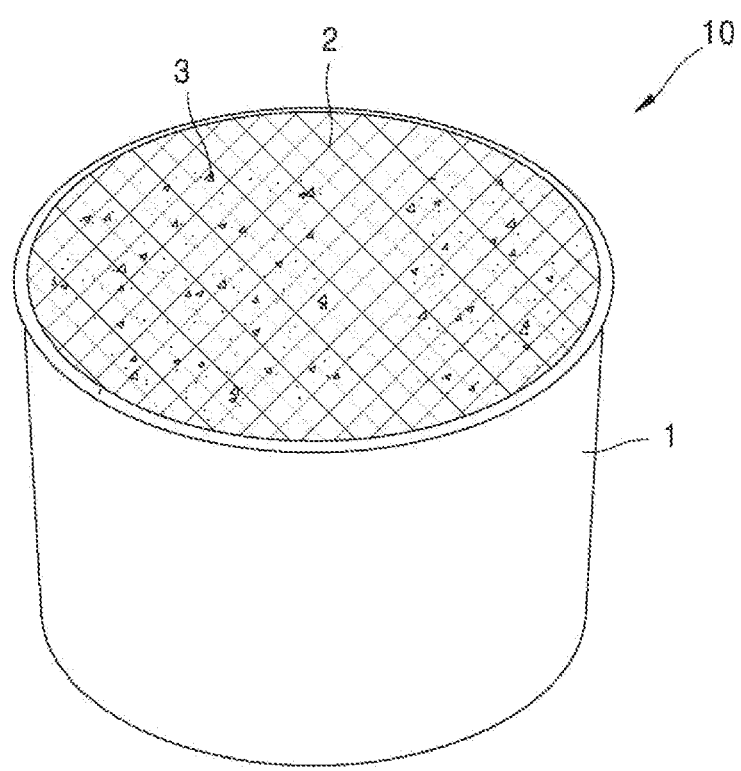

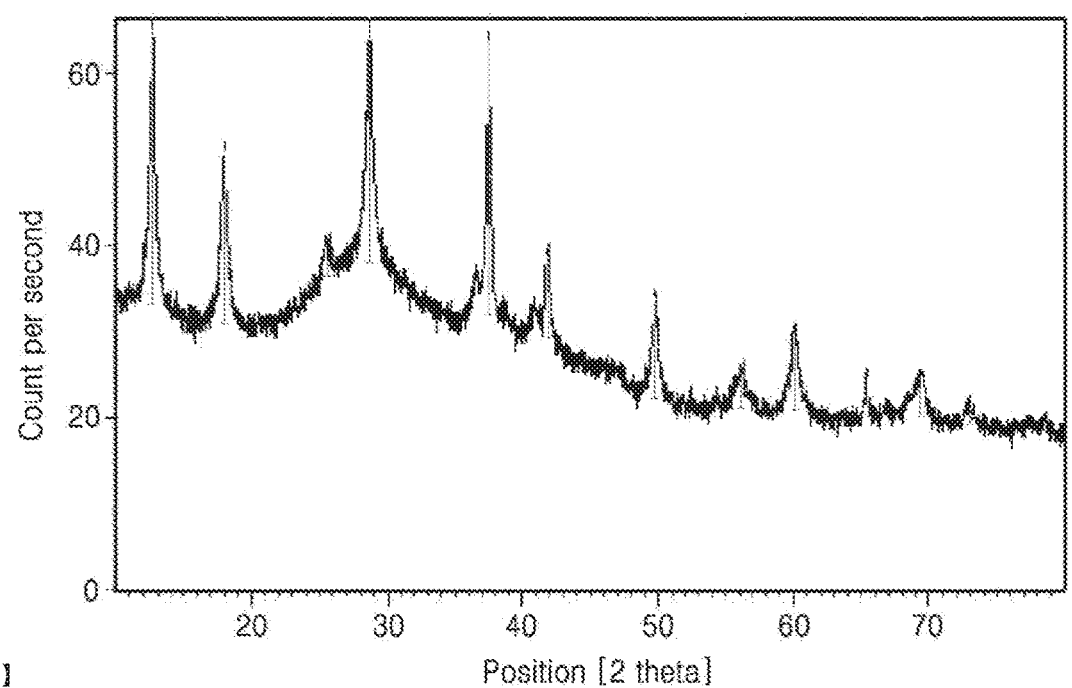
[Figure 2]

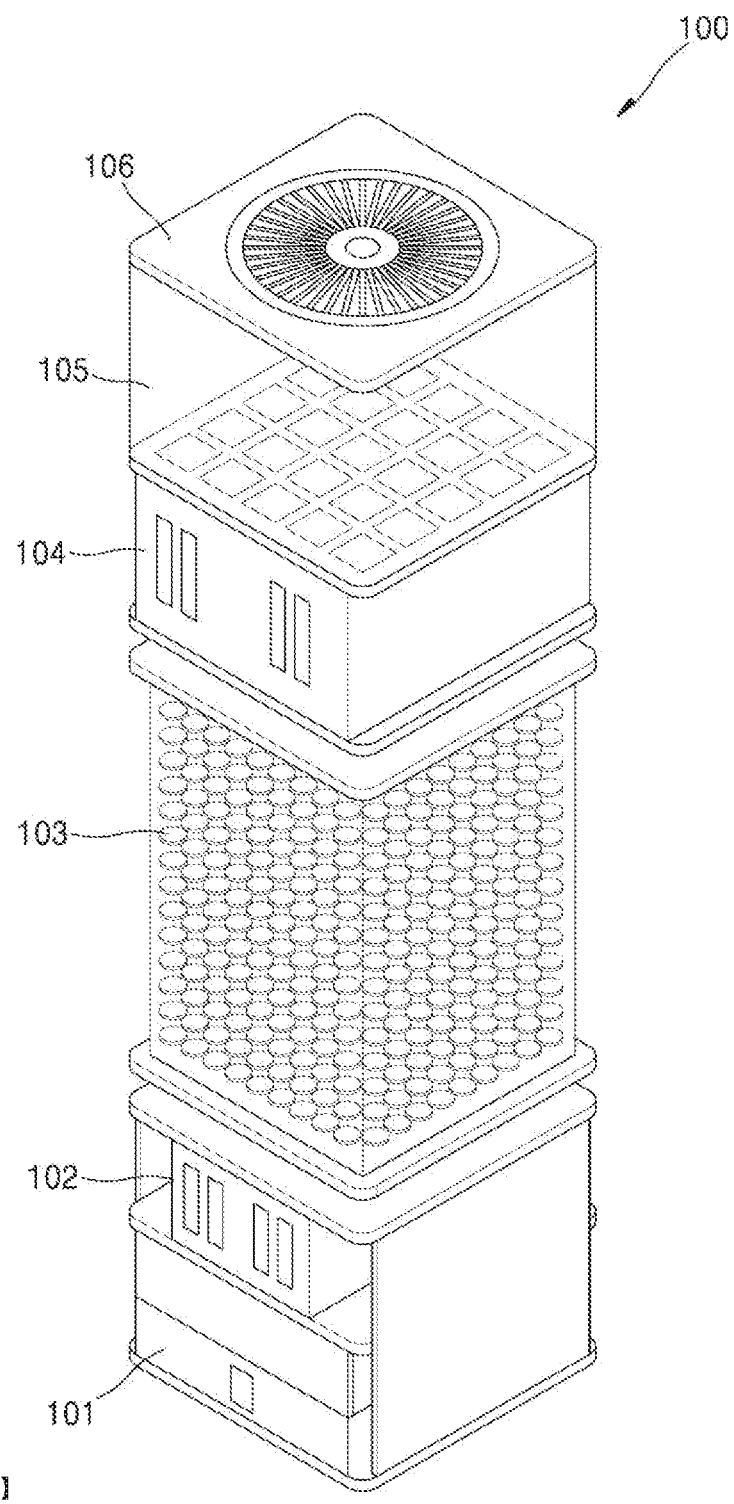
[Figure 3a]

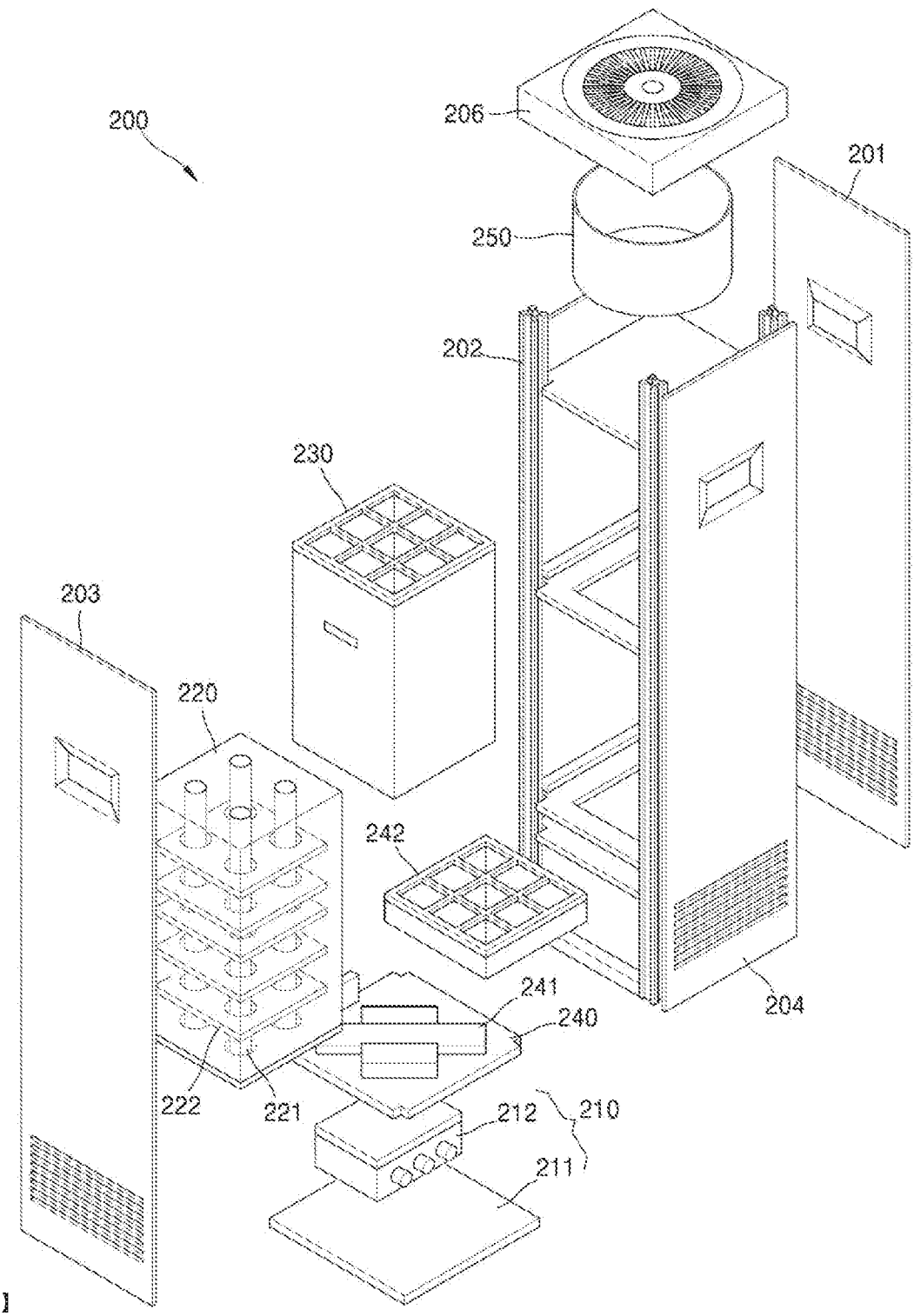
[Figure 3b]

[Figure 4]
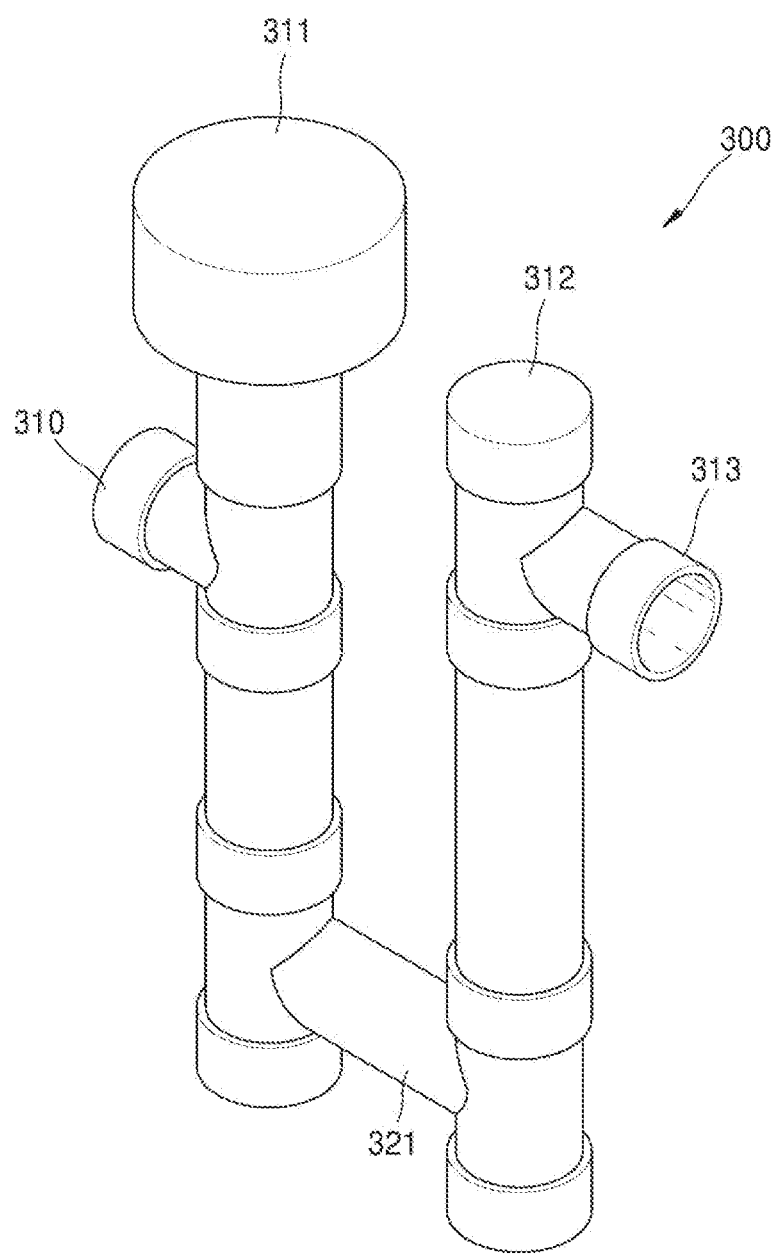

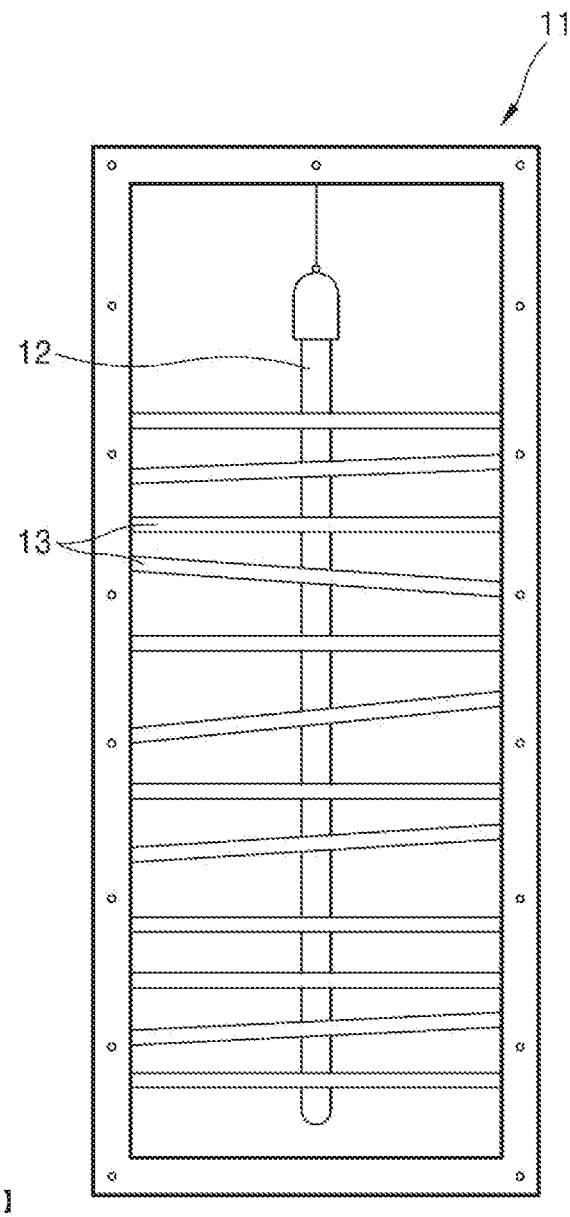
[Figure 5a]

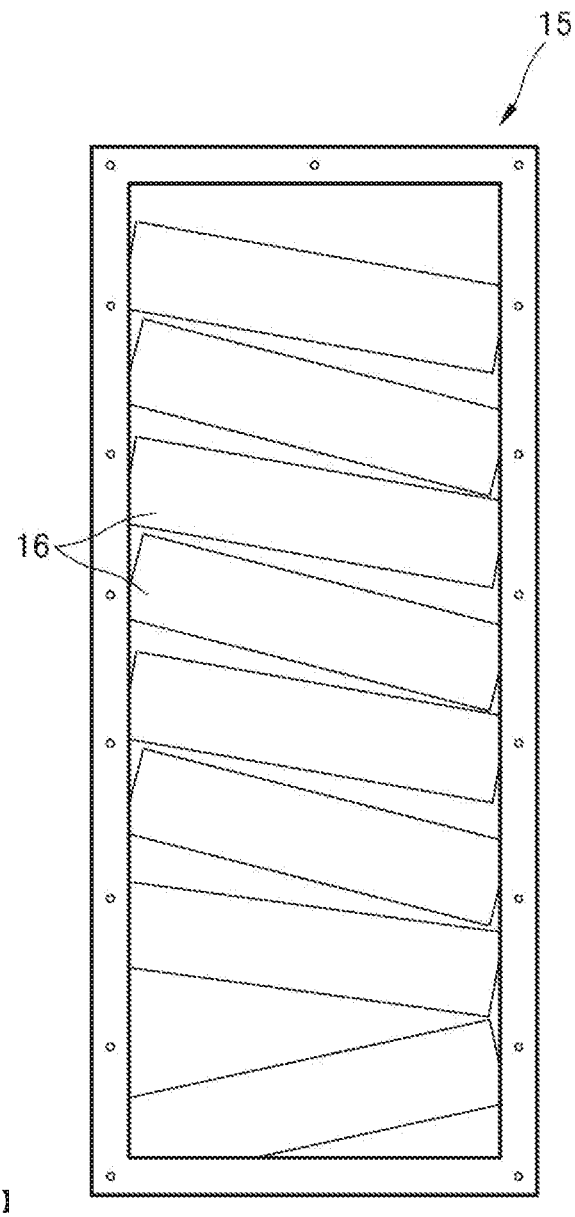
[Figure 5b]

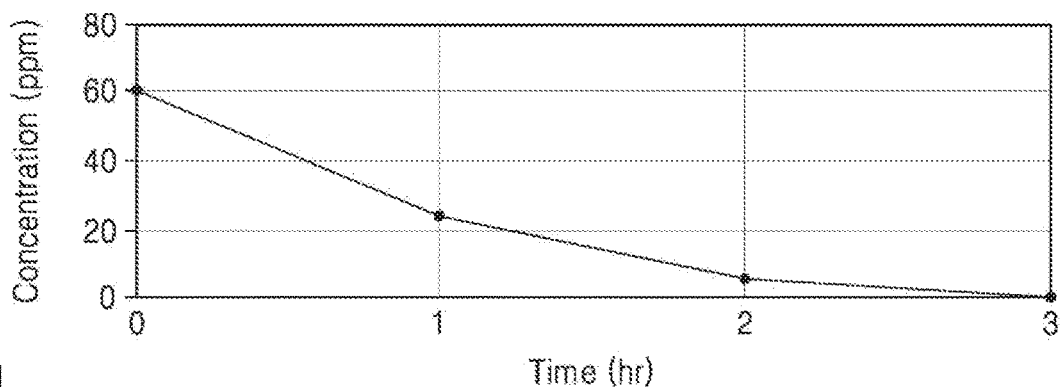
[Figure 6]
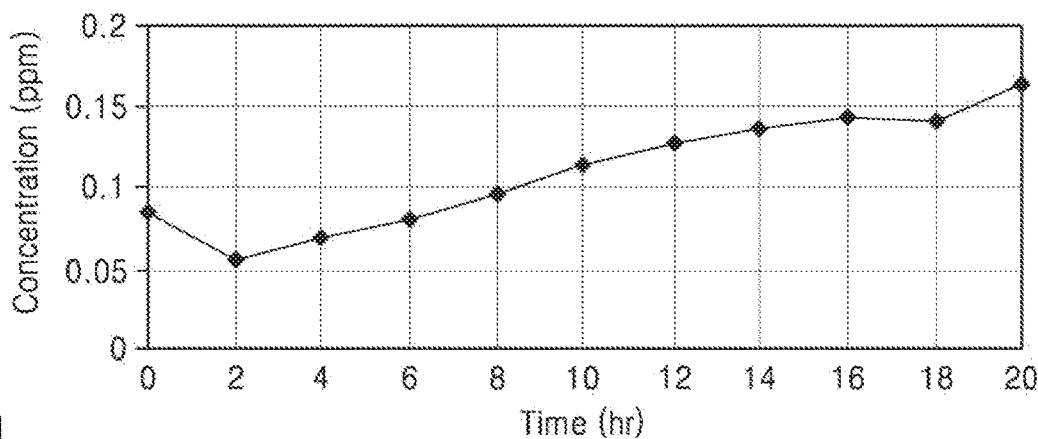
[Figure 7]
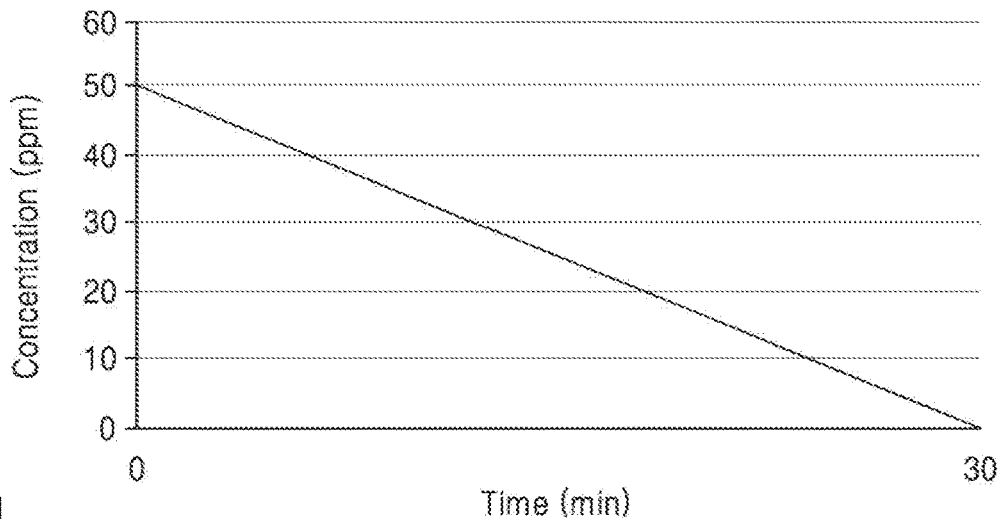
[Figure 8]

[Figure 9]
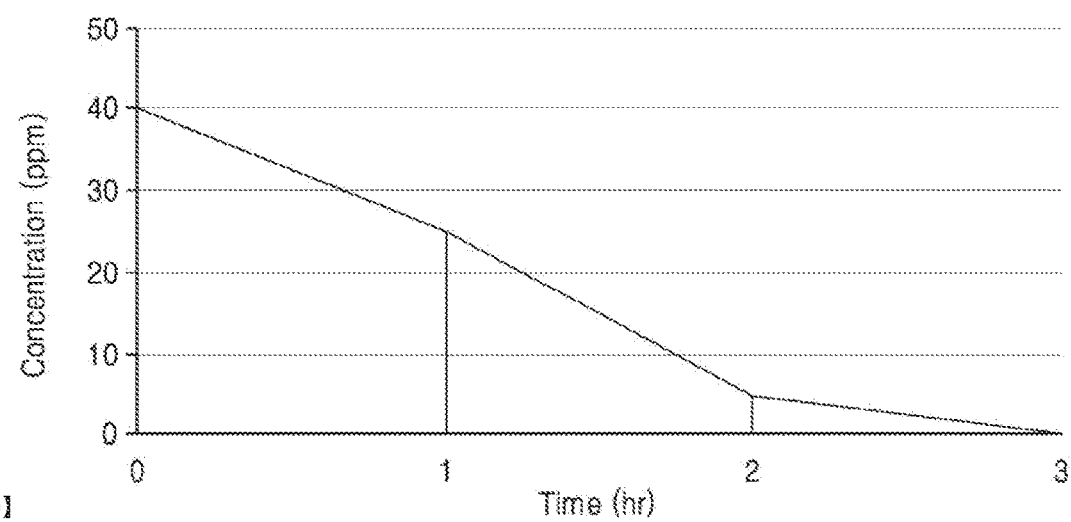

CATALYST STRUCTURE FOR OZONE DECOMPOSITION

CROSS REFERENCE TO RELATED APPLICATIONS

This is the U.S. National Stage of International Application No. PCT/KR2019/007523, filed Jun. 21, 2019, which in turn claims the benefit of Korean Patent Application No. 10-2018-0095103, filed Aug. 14, 2018, which applications are incorporated herein in their entireties.

TECHNICAL FIELD

One or more embodiments relate to a catalyst structure for ozone decomposition, an air-cleaning method using the same, and an air-cleaning device and an air-cleaning system each including the catalyst structure for ozone decomposition.

BACKGROUND ART

Agricultural products such as fruits and vegetables stored in a storeroom secrete and release ethylene gas that serves as a ripening hormone. The released ethylene gas causes agricultural products and/or plants around it to wither, as well as harvested agricultural products. Ethylene gas may be eliminated by a method using a platinum catalyst, a method using potassium permanganate ($KMnO_4$), or a method using a photocatalyst.

Among these, as an example of the method using a photocatalyst, there is known a method using a photocatalyst and a photocatalyst reactor including a UV light source that emits light with a wavelength of 400 nm or less.

However, the photocatalyst may use a light source that has a short wavelength to increase the activity of the photocatalyst. Such a light source is not only harmful to the human body but also has a problem in that, due to the very high energy density of the light source, it generates ozone, a harmful substance converted from oxygen in the air.

Therefore, there is a need to develop a catalyst structure for ozone decomposition that cleans air by increasing the activity of a photocatalyst that eliminates hazardous gas such as ethylene gas and simultaneously decomposes generated ozone, an air-cleaning method using the same, and an air-cleaning device and an air-cleaning system each including the catalyst structure for ozone decomposition.

DISCLOSURE

Technical Problem

One or more embodiments include a catalyst structure for ozone decomposition for cleaning air by decomposing ozone generated during a process of reducing or eliminating hazardous gas including ethylene and harmful bacteria.

One or more embodiments include a method of cleaning air by reducing or eliminating hazardous gas including ethylene and harmful bacteria while simultaneously decomposing ozone generated from the hazardous gas.

One or more embodiments include an air-cleaning device capable of continuously reducing or eliminating constantly generated hazardous gases including ethylene, harmful bacteria, and ozone without replacing a filter.

One or more embodiments include an air-cleaning system including an air-cleaning device containing the catalyst structure for ozone decomposition.

Technical Solution

Additional aspects will be set forth in part in the description which follows and, in part, will be apparent from the description, or may be learned by practice of the presented embodiments.

According to one or more embodiments, a catalyst structure for ozone decomposition, the catalyst structure includes:

a support including a porous inorganic material; and an $\alpha$-$MnO_2$ catalyst on at least a portion of inner pores and a surface of the support.

The porous inorganic material may include a porous ceramic material.

The porous inorganic material may include a porous ceramic material containing 50% or more MgO, $SiO_2$, and $Al_2O_3$ components.

The porous ceramic material may further include an alkali metal oxide.

The support may be a monolith.

The support may further include a material selected from glass, metal, plastic, or any combination thereof.

The $\alpha$-$MnO_2$ catalyst may be fixed to the inner pores and the surface of the support in a binder-free state.

An amount of the $\alpha$-$MnO_2$ catalyst may be in the range of about 1 part by weight to about 10 parts by weight based on 100 parts by weight of the support.

The $\alpha$-$MnO_2$ catalyst may include $\alpha$-$MnO_2$ particles with a diameter of about 50 nm to about 5 μm.

The catalyst structure for ozone decomposition may further include a catalyst selected from $\beta$-$MnO_2$, $\gamma$-$MnO_2$, amorphous $MnO_2$, activated carbon, or any combination thereof.

According to one or more embodiments, a method of cleaning air includes:

a first process of reducing hazardous gas including ethylene and harmful bacteria contained in the air using a photocatalyst reactor; and a second process of decomposing ozone generated in the first process by using the above-described catalyst structure for ozone decomposition.

The photocatalyst reactor may include a vacuum UV lamp and one or more photocatalyst structures arranged around the vacuum UV lamp.

The vacuum UV lamp may include a UV-C lamp that emits light of wavelengths of 254 nm and 185 nm in a ratio of 9:1.

The photocatalyst structure may include a substrate and a $TiO_2$ photocatalyst arranged on the substrate.

The hazardous gas may include organic or inorganic hazardous gas including ethylene, ammonia, acetaldehyde, or any combination thereof.

The harmful bacteria may include *Aspergillus brasilliensis, Escherichia coli, Pseudomonas aeruginosa, Staphylococcus aureus* subsp. *aureus*, or any combination thereof.

The catalyst structure for ozone decomposition may include at least one catalyst structure.

According to one or more embodiments, an air-cleaning device includes:

in a housing, a control area;

an air inlet region;

a first reaction chamber including a vacuum UV lamp and one or more photocatalyst structures arranged around the vacuum UV lamp;

a second reaction chamber in which the above-described catalyst structure for ozone decomposition is located; and an air outlet region.

Air may flow into or out of the air-cleaning device in one direction.

A fan may be installed in at least one of the air inlet region and the air outlet region.

The catalyst structure for ozone decomposition may include at least one catalyst structure.

The air inlet may further include a prefilter.

According to one or more embodiments, an air-cleaning system includes an air-cleaning device containing the above-described catalyst structure for ozone decomposition.

Advantageous Effects

The catalyst structure for ozone decomposition prepared according to an embodiment, which includes the support containing the porous inorganic material and an $\alpha$-$MnO_2$ catalyst located on at least one portion of inner pores or a surface of the support, may clean air by decomposing ozone generated during the process of reducing or eliminating hazardous gas including ethylene and harmful bacteria. Also, provided is the method of cleaning air by decomposing ozone simultaneously reducing or eliminating hazardous gas including ethylene and harmful bacteria. Also, provided is an air-cleaning device and an air-cleaning system capable of continuously reducing or eliminating constantly generated hazardous gas including ethylene, harmful bacteria, and ozone without replacing a filter.

DESCRIPTION OF DRAWINGS

These and/or other aspects will become apparent and more readily appreciated from the following description of the embodiments, taken in conjunction with the accompanying drawings in which:

FIG. 1 is a schematic diagram illustrating a catalyst structure for ozone decomposition, according to an embodiment;

FIG. 2 is a graph illustrating results of XRD analysis of an $\alpha$-$MnO_2$ catalyst of a catalyst structure for ozone decomposition according to Example 1;

FIG. 3A is a schematic diagram of an air-cleaning device according to an embodiment;

FIG. 3B is a schematic partially exploded perspective view of an air-cleaning device according to an embodiment;

FIG. 4 is a schematic view of an inner portion of an air-cleaning device according to an embodiment;

FIG. 5A is a schematic view of the inside of a first reaction chamber of an air-cleaning device according to an embodiment;

FIG. 5B is a schematic view of the inside of a second reaction chamber of an air-cleaning device according to an embodiment;

FIG. 6 is a graph illustrating results of evaluation of the ability of an air-cleaning device manufactured according to Example 2 to reduce ethylene gas when a catalyst structure for ozone decomposition prepared according to Example 1 is not installed in a second reaction chamber;

FIG. 7 is a graph illustrating results of evaluation of the ability of a catalyst structure for ozone decomposition according to Example 1 in a second reaction chamber to decompose ozone generated and accumulated during a process of eliminating ethylene gas and the like performed in a first reaction chamber of an air-cleaning device manufactured according to Example 2;

FIG. 8 is a graph illustrating results of evaluation of the ability of the air-cleaning device manufactured according to Example 2 to reduce ammonia gas when a catalyst structure for ozone decomposition prepared according to Example 1 is not installed in a second reaction chamber; and FIG. 9 is a graph illustrating results of evaluation of the ability of the air-cleaning device manufactured according to Example 2 to reduce acetaldehyde gas when a catalyst structure for ozone decomposition prepared according to Example 1 is not installed in a second reaction chamber.

MODE FOR INVENTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, a catalyst structure for ozone decomposition, an air-cleaning method using the same, and an air-cleaning device and an air-cleaning system each including the catalyst structure for ozone decomposition according to example embodiments will be described in more detail with reference to the accompanying drawings. The following descriptions are for the purpose of describing particular embodiments and the present disclosure is not limited thereby. The present disclosure is only defined by the scope of claims below. Also, in the specification and drawings, like reference numerals will be assigned to like parts or components having substantially same functions and repeated descriptions are omitted.

Throughout the specification, the term "comprising" or "including" is intended to indicate that an element do not preclude the other elements but further add and/or intervene another element, unless otherwise stated.

FIG. 1 is a schematic diagram illustrating a catalyst structure for ozone decomposition 10 according to an example embodiment.

Referring to FIG. 1, the catalyst structure for ozone decomposition 10, the catalyst structure may include: a support 1 containing a porous inorganic material; and an $\alpha$-$MnO_2$ catalyst 3 located on at least one portion of inner pores 2 and a surface of the support 1.

A sufficient amount of a binder is required for coating of the $\alpha$-$MnO_2$ catalyst 3 on an organic support such as a fiber aggregate commonly available, resulting in a decrease in the activity of the $\alpha$-$MnO_2$ catalyst 3. Also, because the organic support such as the fiber aggregate is deformed by an external environment such as strong acid, high temperature, and strong wind due to flexible properties thereof, there is a need for a separate design to fix the support 1.

The support 1 including the porous inorganic material of the catalyst structure for ozone decomposition according to an embodiment has a wider specific surface area than a support including an organic material such as polybenzimidazole or polyimide and exhibits high $\alpha$-$MnO_2$ catalyst activity. In addition, the support 1 including the porous inorganic material may maintain the shape thereof against the external environment such as strong acid, high temperature, and strong wind.

Manganese dioxide may exist in different crystal such as including α-, β-, γ-, δ-, and λ-types. Among them, the α-MnO$_2$ catalyst 3 has a structure with abundant oxygen vacancies related to ozone decomposition, thereby having high catalytic activity for decomposition of ozone, compared to manganese dioxide having different crystal structures. The α-MnO$_2$ catalyst 3 may be prepared by precipitating MnO$_2$ via a reaction between a starting material, such as an aqueous solution of manganese chloride (MnCl$_2$.4H$_2$O), manganese acetate (Mn(CH$_3$COO)$_2$.4H$_2$O), or manganese sulfate (MnSO$_4$.5H$_2$O), and a given equivalent weight of KMnO$_4$ at room temperature, and precipitating the MnO$_2$ in a hydrothermal reactor.

The porous inorganic material may include a porous ceramic material.

For example, the porous inorganic material may include a porous ceramic material containing 50% or more MgO, SiO$_2$, and Al$_2$O$_3$ components. The porous ceramic material may have a ceramic honeycomb structure. The porous ceramic material may include about 100 to about 500, for example, about 200 to about 500, for example, about 300 to about 400 square cells per inch. Air or the like may flow into the porous ceramic material through the square cells.

The porous ceramic material may increase the catalytic activity due to a high strength and a large specific surface area. In addition, the porous ceramic material may lower a pressure loss due to high air permeability and may maintain the shape thereof against an experimental environment such as strong acid, high temperature, and strong wind.

A cross-section of the porous ceramic material may have various shapes such as a circular, oval, rectangular, or square shape. The porous ceramic material may have, for example, a cylindrical, rectangular parallelepiped, or cubic shape with a height and a diameter each of several millimeters (mm) to several tens of millimeters (mm). However, the embodiment is not limited thereto, and any porous ceramic materials with various shapes available to one or ordinary skill in the art may be used.

The porous ceramic material may further include an alkali metal oxide. Examples of the alkali metal oxide may include Li$_2$O, Na$_2$O, and K$_2$O. The porous ceramic material further including the alkali metal oxide may enable the catalyst structure for ozone decomposition to maintain the shape without thermal deformation even at a high temperature.

The support 1 may be a monolith.

The support 1 may further include a material selected from glass, metal, plastic, or any combination thereof.

The α-MnO$_2$ catalyst 3 may be fixed to the inner pores and the surface of the support 1 in a binder-free state. For example, the α-MnO$_2$ catalyst 3 in the form of particles may be fixed to the inner pores and the surface of the support 1 without a binder, thereby increasing the catalytic activity.

An amount of the α-MnO$_2$ catalyst 3 may be in the range of about 1 part by weight to about 10 parts by weight based on 100 parts by weight of the support 1. For example, the amount of the α-MnO$_2$ catalyst 3 may be in the range of about 2 parts by weight to about 9 parts by weight, for example, about 2 parts by weight to about 8 parts by weight, for example, about 2 parts by weight to about 7 parts by weight, based on 100 parts by weight of the support 1.

When the amount of the α-MnO$_2$ catalyst 3 is within the above range, a coating solution containing the α-MnO$_2$ catalyst 3 may be easily applied to the support 1 including the porous inorganic material to a sufficient amount for the catalytic activity, and the inner pores of the support 1 including the porous inorganic material may not be blocked.

The α-MnO$_2$ catalyst 3 may include α-MnO$_2$ particles with a diameter of about 50 nm to about 5 μm. The α-MnO$_2$ catalyst 3 may include α-MnO$_2$ particles with a diameter of, for example about 60 nm to about 4 μm, for example about 70 nm to 3 about μm, for example about 80 nm to about 3 μm.

Within the diameter ranges, the α-MnO$_2$ catalyst 3 may be easily coated on the support 1 including the porous inorganic material using the coating solution containing the α-MnO$_2$ catalyst 3, and the α-MnO$_2$ catalyst 3 may not be separated from the support 1 including the porous inorganic material and have catalytic activity maintained at a high level after coating.

The catalyst structure for ozone decomposition may further include a catalyst selected from β-MnO$_2$, γ-MnO$_2$, amorphous MnO$_2$, activated carbon, or any combination thereof.

A method of cleaning air according to another embodiment may include: a first process of reducing hazardous gas including ethylene and harmful bacteria in the air using a photocatalyst reactor; and a second process of decomposing ozone generated in the first process by using the above-described catalyst structure for ozone decomposition.

The air-cleaning method may include a process of reducing or eliminating hazardous gas including ethylene and harmful bacteria (first process) and a process of decomposing ozone generated in the first process (second process). The air-cleaning method according to an embodiment may provide a method of reducing and even eliminating the hazardous gas including ethylene and harmful bacteria by the first and second processes even when air containing hazardous gas including ethylene and harmful bacteria is introduced without generating ozone.

The photocatalyst reactor may include a vacuum ultraviolet (UV) lamp and one or more photocatalyst structures arranged around the vacuum UV lamp.

For example, the photocatalyst reactor may include an UV-C lamp and one or more photocatalyst structures arranged around the UV-C lamp. The UV-C lamp may consist of wavelengths of 254 nm and 185 nm in a ratio of 9:1. When the UV-C lamp with an output power of 16 W was used within the wavelength ratio described above, the ability to reduce or eliminate hazardous gas including ethylene and harmful bacteria which are difficult to be decomposed by the photocatalyst may further be improved. The ability to reduce or eliminate hazardous gas including ethylene and harmful bacteria may further be improved by appropriately adjusting the number, voltage, current, or output power of the UV-C lamp.

The photocatalyst structure may include a substrate and a TiO$_2$ photocatalyst located on the substrate. Examples of the substrate may be, but are not limited to, a 3-dimensional stainless-steel net or a transparent glass tube each coated with the TiO$_2$ photocatalyst. In this regard, a coating method may be, but is not limited to, dip coating.

The hazardous gas may include organic or inorganic hazardous gas including ethylene, ammonia, acetaldehyde, or any combination thereof. The harmful bacteria may include *Aspergillus brasilliensis, Escherichia coli, Pseudomonas aeruginosa, Staphylococcus aureus* subsp. *aureus*, or any combination thereof. The hazardous gas or harmful bacteria may be reduced to a trace amount or eliminated after several tens of minutes to several hours or several tens of hours by the first process, Oxygen in the air is converted into ozone in the first process resulting in generation of excess ozone, and the ozone may be eliminated while passing through the above-described catalyst structure for ozone decomposition in the second process, and thus cleaned air from which the ozone is eliminated may be released. The catalyst structure for ozone decomposition is as described above, and thus detailed descriptions thereof will be omitted.

The catalyst structure for ozone decomposition may include at least one catalyst structure, for example 2 or more, 3 or more, 4 or more, 5 or more, 6 or more, 7 or more, or S or more catalyst structures. As the number of the catalyst structures for ozone decomposition increases, the ability to decompose ozone may further be improved.

FIG. 3A is a schematic diagram of an air-cleaning device 100 according to an embodiment.

Referring to FIG. 3A, the air-cleaning device 100 according to an embodiment includes, in a housing, a control area 101; an air inlet region 102; a first reaction chamber 103 including a vacuum UV lamp and one or more photocatalyst structures arranged around the vacuum UV lamp; a second reaction chamber 104 in which the above-described catalyst structure for ozone decomposition is located; and air outlet region 105.

Air may flow into or out of the air-cleaning device 100 in one direction. Referring to FIG. 3A, air may How into or out of the air-cleaning device 100 through openings such as voids or holes upward from a lower portion.

A fan 106 may be installed on at least one of the air inlet region 102 and the air outlet region 105. Referring to FIG. 3A, the fan 106 is installed on an upper surface of the air outlet region 105. The air outlet region 105 may serve as a storage space for storing cleaned air.

FIG. 3B is a schematic partially exploded perspective view of an air-cleaning device 200 according to an embodiment.

Referring to FIG. 3B, the air-cleaning device 200 according to an embodiment includes, in a housing 201, 202, 203, and 204, a control area 210 provided with a circuit board 211 and a circuit breaker 212; an air inlet region 102 in which a mesh-type second support 242 and a prefilter 241 located on a first support 240 are located; a first reaction chamber 230 in which an UV-C lamp 221 and a plurality of photocatalyst structures 222 arranged around the UV-C lamp 221 are located; a second reaction chamber 220 in which the above-described catalyst structure for ozone decomposition is located; an air outlet region 250; and a fan 206 installed on an upper surface of the air outlet region 250.

The control area 210, the air inlet region 102, the first reaction chamber 230, the second reaction chamber 220, and the air outlet region 250 are separated from one another by barrier walls with openings. The circuit board 211 and circuit breaker 212 located in the control area 210 is electrically connected to both the UV-C lamp 221 of the first reaction chamber 230 and the fan 206 on the upper surface of the air outlet region 250. The prefilter 240 may be, for example, a non-woven fabric. However, the embodiment is not limited thereto and any prefilter material available in the art may also be used.

FIG. 4 is a schematic view of an inner portion of an air-cleaning device 300 according to an embodiment.

Referring to FIG. 4, the air-cleaning device 300 includes an air inlet region 310; a first reaction chamber 311 in which an UV-C lamp and one of more photocatalyst structures arranged around the UV-C lamp are located; a second reaction chamber 312 connected to the first reaction chamber 311 and including the above-described catalyst structure for ozone decomposition; and air outlet region 313.

The first reaction chamber 311 may be connected to the second reaction chamber 312 via a connection pipe 321.

A fan may be installed on at least one of the air inlet region 310 and the air outlet region 113.

The air inlet region 310 may be fixedly located on one surface of the first reaction chamber 311 in the form of an air inlet or installed in a container separated from the first reaction chamber 311. The air outlet region 313 may be fixedly located on one surface of the second reaction chamber 312 or installed in a container separated from the second reaction chamber 312. The first reaction chamber 311 and/or the second reaction chamber 312 may be respectively provided with a storage container(s) configured to store air and the like flowing from the first reaction chamber 311 and/or the second reaction chamber 312 and connected via the connection pipe.

Each of the UV-C lamp in the first reaction chamber 111 and the fan installed on the air outlet region 313 may be connected to a power source.

FIG. 5A is a schematic view of the inside of a first reaction chamber 11 of an air-cleaning device manufactured according to an embodiment. FIG. 5B is a schematic view of the inside of a second reaction chamber 15 of an air-cleaning device manufactured according to an embodiment.

Referring to FIG. 5A, an UV-C lamp 12 and one or more photocatalyst structures 13 randomly arranged around the UV-C lamp 12 are located in the first reaction chamber 11. Referring to FIG. 5B, a plurality of catalyst structure for ozone decompositions 16 are stacked in the second reaction chamber 15.

An air-cleaning system according to another embodiment may include an air-cleaning device containing the above-described catalyst structure for ozone decomposition. The air-cleaning system may further include a controller, a temperature controller, and the like, as required.

Hereinafter, one or more embodiments will be described in detail with reference to the following examples and comparative examples. However, these examples are not intended to limit the purpose and scope of the one or more embodiments.

EXAMPLES

Preparation of Catalyst Structure for Ozone Decomposition

Example 1: Preparation of Catalyst Structure for Ozone Decomposition 39.4 g of $MnCl_2 \cdot 4H_2O$ and 31.6 g of $KMnO_4$ were added to 250 mL of water and stirred to obtain a mixture solution. 250 mL of the mixture solution was heated to 220° C. for 2 hours in a hydrothermal reactor and a reaction was proceeded at 220° C. for 3 hours, and then the mixture solution was filtered. Obtained precipitates were dried at 100° C. for 2 hours to obtain $\alpha$-$MnO_2$ in a bulk state. An $\alpha$-$MnO_2$-containing solution (solid content of about 10%) prepared by dispersing the $\alpha$-$MnO_2$ in the bulk state in water was milled to obtain an $\alpha$-$MnO_2$ dispersion including $\alpha$-$MnO_2$ particles having an average diameter D50 of 2.5 μm.

A round-shaped porous cordierite monolith including MgO, $SiO_2$, and $Al_2O_3$ components in an amount of 50% or more and having a diameter of 93 mm and a height of 50 mm (93λ50 mm/300 cpsi, manufactured by Ceracomb Co., Ltd.) was prepared. The porous cordierite monolith was dipped in the $\alpha$-$MnO_2$ dispersion and dried to prepare a catalyst structure for ozone decomposition in which the $\alpha$-$MnO_2$ particles are coated on the inner pores and the surface of the porous cordierite monolith as shown in FIG. 1.

In this case, the amount of the α-$MnO_2$ catalyst was 5 parts by weight based on 100 parts by weight of the porous cordierite monolith.

Comparative Example 1: Porous Cordierite Monolith

A round-shaped porous cordierite monolith including MgO, $SiO_2$, and $Al_2O_3$ components in an amount of 50% or more and having a diameter of 93 mm and a height of 50 mm (93λ50 mm/300 cpsi, manufactured by Ceracomb Co., Ltd.) was prepared.

Comparative Example 2: Preparation of Catalyst Structure for Ozone Decomposition 39.4 g of $MnCl_2 \cdot 4H_2O$ and 31.6 g of $KMnO_4$ were added to 250 mL of water and stirred to obtain a mixture solution. 250 mL of the mixture solution was heated to 220° C. for 2 hours in a hydrothermal reactor and a reaction was proceeded at 220° C. for 3 hours, and then the mixture solution was filtered. Obtained precipitates were dried at 100° C. for 2 hours to obtain α-$MnO_2$ in a bulk state. 50 g of α-$MnO_2$ in the bulk state was surrounded by nylon mesh to prepare a catalyst structure for ozone decomposition.

Comparative Example 3: Preparation of Catalyst Structure for Ozone Decomposition A catalyst structure for ozone decomposition was prepared in the same manner as in Comparative Example 2, except that 100 g of α-$MnO_2$ in the bulk state was used instead of 50 g of α-$MnO_2$ in the bulk state.

Comparative Example 4: Preparation of Catalyst Structure for Ozone Decomposition A catalyst structure for ozone decomposition was prepared in the same manner as in Comparative Example 2, except that 200 g of α-$MnO_2$ in the bulk state was used instead of 50 g of α-$MnO_2$ in the bulk state.

Comparative Example 5: Preparation of Catalyst Structure for Ozone Decomposition A catalyst structure for ozone decomposition was prepared in the same manner as in Comparative Example 2, except that 270 g of α-$MnO_2$ in the bulk state was used instead of 50 g of α-$MnO_2$ in the bulk state.

Comparative Example 6: Preparation of Catalyst Structure for Ozone Decomposition A catalyst structure for ozone decomposition was prepared in the same manner as in Comparative Example 2, except that 312 g of α-$MnO_2$ in the bulk state was used instead of 50 g of α-$MnO_2$ in the bulk state.

Manufacture of Air-Cleaning Device

Example 2: Manufacture of Air-Cleaning Device

An air cleaning experiment was conducted in a chamber space of 1 m×1 m×1 m, and an air-cleaning device 300 for the experiment was manufactured as shown in FIG. 4.

At the center of the first reaction chamber 311 provided with an air inlet 310 (including a fan) at one surface, an UV-C lamp (consisting of wavelengths of 254 nm and 185 nm in a ratio of 9:1 with an output power of 16 W, GPH357T5VH/4P, manufactured by Light Sources Inc.) was located, and photocatalyst filters prepared by coating a $TiO_2$ photocatalyst on the surface and inside of a stainless-steel net were randomly arranged around the UV-C lamp. The $TiO_2$ used in the photocatalyst filter was Degussa P25 $TiO_2$ (75% anatase/25% rutile; manufactured by Nippon Aerosil Co., Ltd., and the stainless-steel used is a continuous structure with multiple layers of mesh stainless-steel nets each having a size of 2 mm×2 mm and a circular hole into which the UV-C lamp is inserted such that the mesh stainless-steel nets are spaced apart from each other at regular intervals along a longitudinal direction and arranged in a zigzag shape by bending a central portion of each circular hole, and the coating is conducted by dip coating.

In the second reaction chamber 312, 8 catalyst structures for ozone decomposition manufactured according to Example 1 were stacked. The first reaction chamber 311 was connected to the second reaction chamber 312 via the connection pipe 321 which was used as a passage for air including ozone generated in the first reaction chamber and flowing into the second reaction chamber. The air outlet 313 was installed at one surface of the second reaction chamber 312 and cleaned air was discharged therethrough. In this regard, a fan was installed on the air outlet 313.

Also, the UV-C lamp in the first reaction chamber 311 and the fan installed on the air outlet region 313 were connected to a power source, respectively.

Example 3: Manufacture of Air-Cleaning Device

An air-cleaning device was manufactured in the same manner as in Example 2, except that an UV-C lamp (consisting of wavelengths of 254 nm and 185 nm in a ratio of 9:1 with an output power of 25 W) was used instead of the UV-C lamp (consisting of wavelengths of 254 nm and 185 nm in a ratio of 9:1 with an output power of 16 W) at the center of the first reaction chamber 311.

Examples 4 to 10: Manufacture of Air-Cleaning Device

Air-cleaning devices were manufactured in the same manner as in Example 2, except that 1 to 7 catalyst structures for ozone decomposition prepared according to Example 1 were respectively stacked in the second reaction chamber 312.

Comparative Example 7: Manufacture of Air-Cleaning Device

An air-cleaning device was manufactured in the same manner as in Example 2, except that an UV-C lamp (with an UV wavelength of 365 nm and an output power of 15 W) was used instead of the UV-C lamp (consisting of wavelengths of 254 nm and 185 nm in a ratio of 9:1 with an output power of 16 W) at the center of the first reaction chamber 311.

Comparative Example 8: Manufacture of Air-Cleaning Device

An air-cleaning device was manufactured in the same manner as in Example 2, except that an UV-C lamp (with an UV wavelength of 254 nm and an output power of 8 W) was used instead of the UV-C lamp (consisting of wavelengths of 254 nm and 185 nm in a ratio of 9:1 with an output power of 16 W) at the center of the first reaction chamber 311.

Comparative Example 9: Manufacture of Air-Cleaning Device

An air-cleaning device was manufactured in the same manner as in Example 2, except that the porous cordierite monolith prepared according to Comparative Example 1 was used instead of the catalyst structure for ozone decomposition prepared according to Example 1.

Comparative Examples 10 to 14: Manufacture of Air-Cleaning Device

Air-cleaning devices were manufactured in the same manner as in Example 2, except that the catalyst structures for ozone decomposition prepared according to Comparative Examples 2 to 6 were respectively used in the second reaction chamber 312 instead of the catalyst structure for ozone decomposition prepared according to Example 1.

Analysis Example 1: X-Ray Diffraction (XRD) Data—Component Analysis of α-MnO$_2$-Containing Layer An XRD test was performed on the α-MnO$_2$ catalyst of the catalyst structure for ozone decomposition according to Example 1. The α-MnO$_2$ catalyst dispersion synthesized by hydrothermal synthesis was filtered and dried to obtain powder, and the obtained powder was tested by XRD. The results are shown in FIG. 2.

A Rigaku RINT2200HF+ diffractometer using CuKα radiation (1.540598 Å) was used as an XRD analyzer.

Referring to FIG. 2, the α-MnO$_2$ catalyst of the catalyst structure for ozone decomposition prepared according to Example 1 showed distinct peaks at diffraction angles (2Θ) of about 13°, about 18°, about 29°, about 37°, and about 60°. Accordingly, it may be confirmed that the α-MnO$_2$ catalyst of the catalyst structure for ozone decomposition is pure α-MnO$_2$.

Evaluation Example 1: Evaluation of Ability to Reduce Hazardous Gas (1) Evaluation of Ability to Reduce Ethylene Gas Ethylene was filled in a chamber space of 1 m×1 m×1 m in a given concentration, and evaluation of the ability of each of the air-cleaning devices manufactured according to Example 2, Example 3, Comparative Example 7, and Comparative Example 8 was conducted by operating the air-cleaning device without the catalyst structure for ozone decomposition prepared according to Example 1 in the second reaction chamber to evaluate the ability to reduce ethylene gas. Concentrations of ethylene remaining in the chamber space were measured with the elapse of operating time of the respective air-cleaning devices and the results are shown in FIG. 5, Table 1, and Table 2, respectively.

TABLE 1

| Time (min) | Ethylene Concentration (ppm) Example 3 |
|---|---|
| 0 | 54 |
| 10 | 32 |
| 20 | 18 |
| 30 | 6 |
| 40 | 0 |

TABLE 2

| | Ethylene Concentration (ppm) | |
|---|---|---|
| Time (min) | Comparative Example 7 | Comparative Example 8 |
| 0 | 50 | 50 |
| 60 | 50 | 50 |
| 120 | 50 | 50 |
| 180 | 50 | 50 |

Referring to FIG. 5, it was confirmed that ethylene gas was completely eliminated after 6 hours by the air-cleaning device manufactured according to Example 2 when the initial concentration of ethylene gas was 60 ppm.

Referring to Table 1 above, it was confirmed that ethylene gas was completely eliminated after 40 minutes by the air-cleaning device manufactured according to Example 3 when the initial concentration of ethylene gas was 54 ppm. In comparison, referring to Table 2, it was confirmed that the same concentrations of ethylene gas remained even after 180 minutes when the air-cleaning devices according to Comparative Examples 7 and 8 were used and the initial concentration of ethylene gas was 50 ppm.

Therefore, it was confirmed that ethylene gas was completely removed within shorter time by the air-cleaning devices according to Examples 2 and 3 than the air-cleaning devices according to Comparative Examples 7 and 8. Furthermore, the ability of the air-cleaning device manufactured according to Example 3 to eliminate ethylene gas was considerably improved, compared to the air-cleaning device manufactured according to Example 2.

(2) Evaluation of Ability to Reduce Ammonia and Acetaldehyde Gas

The ability of the air-cleaning device manufactured according to Example 2 to reduce each of ammonia and acetaldehyde gas was evaluated without installing the catalyst structure for ozone decomposition prepared according to Example 1 in the second reaction chamber. The results are shown in FIGS. 7 and 8.

Referring to FIG. 7, it was confirmed that ammonia gas was completely eliminated after 30 minutes by the air-cleaning device manufactured according to Example 2 when the initial concentration of ammonia was 50 ppm. Referring to FIG. 8, it was confirmed that acetaldehyde gas was completely eliminated after 3 hours by the air-cleaning device manufactured according to Example 2 when the initial concentration of the acetaldehyde was 40 ppm.

Therefore, it was confirmed that ammonia and acetaldehyde gas was completely eliminated by the air-cleaning device manufactured according to Example 2 within short time.

Evaluation Example 2: Evaluation of Ability to Decompose Ozone (1) Evaluation of Ability to Decompose Ozone 1

The ability of the catalyst structure for ozone decomposition prepared according to Example 1 stacked in the second reaction chamber to decompose ozone, which was generated and accumulated during a process of eliminating ethylene gas and the like in the first reaction chamber of the air-cleaning device manufactured according to Example 2, was evaluated. The results are shown in FIG. 6.

Referring to FIG. 6, the catalyst structure for ozone decomposition prepared according to Example 1 installed in the second reaction chamber included in the air-cleaning device manufactured according to Example 2 exhibited an ozone concentrations of about 0.16 ppm even after 20 hours indicating a high ability to decompose ozone.

(2) Evaluation of Ability to Decompose Ozone 2

In a state where there was no ethylene gas around each of the air-cleaning devices manufactured according to Examples 4 to 10 and Comparative Examples 9 to 14, the ability of each of the catalyst structures for ozone decomposition respectively prepared according to Example 1 and Comparative Examples 2 to 6 and stacked in the second reaction chamber to decompose ozone was evaluated by measuring the concentration of ozone generated by the UV-C lamp installed at the center of the first reaction chamber and accumulated therein. The results are shown in Tables 3 and 4 respectively.

TABLE 3

| | Ozone Concentration (ppm) | | | | | | | |
|---|---|---|---|---|---|---|---|---|
| Time (hour) | Comparative Example 9 | Example 4 | Example 5 | Example 6 | Example 7 | Example 8 | Example 9 | Example 10 |
| 0 | 0.02 | 0.02 | 0.02 | 0.02 | 0.02 | 0.02 | 0.02 | 0.02 |
| 1 | 22.33 | 0.60 | 0.17 | 0.20 | 0.26 | 0.12 | 0.09 | 0.10 |
| 2 | 33.59 | 0.67 | 0.17 | 0.22 | 0.26 | 0.13 | 0.10 | 0.11 |
| 3 | 39.52 | 0.79 | 0.18 | 0.23 | 0.26 | 0.14 | 0.10 | 0.12 |

TABLE 4

| | Ozone Concentration (ppm) | | | | |
|---|---|---|---|---|---|
| Time (hour) | Comparative Example 10 | Comparative Example 11 | Comparative Example 12 | Comparative Example 13 | Comparative Example 14 |
| 0 | 0 | 0 | 0 | 0 | 0 |
| 1 | 23 | 5.2 | 1 | 0.9 | 0.85 |
| 2 | 42 | 6.3 | 1.2 | 1.25 | 1.1 |
| 3 | 46 | 6.7 | 1.5 | 1.5 | 1.25 |
| 4 | 55 | 11.5 | 1.75 | 1.7 | 1.55 |

Referring to Table 3, the catalyst structure for ozone decomposition prepared according to Example 1 and installed in the second reaction chamber included in each of the air-cleaning devices manufactured according to Examples 4 to 10 exhibited an ozone concentration of 0.20 ppm or less after 3 hours, indicating a higher ability to decompose ozone than the catalyst structure for ozone decomposition prepared according to Comparative Example 1 and installed in the second reaction chamber included in the air-cleaning device manufactured according to Comparative Example 9. Also, it was confirmed that as the number of the catalyst structures for ozone decomposition prepared according to Example 1 increases, the ability to decompose ozone is improved.

In comparison, referring to Table 4, all of the catalyst structures for ozone decomposition prepared according to Comparative Examples 10 to 14 respectively installed in the second reaction chambers of the air-cleaning devices manufactured according to Comparative Examples 10 to 14 exhibited ozone concentrations of 1.55 ppm or more even after 4 hours.

Based thereon, it was confirmed that the catalyst structure for ozone decomposition prepared according to Example 1 and installed in the second reaction chamber included in each of the air-cleaning devices according to Examples 4 to 10 had a higher ability to decompose ozone than the catalyst structures for ozone decomposition prepared according to Comparative Examples 1 to 6 installed in the second reaction chamber included in the respective air-cleaning devices manufactured according to Comparative Examples 9 to 14.

Evaluation Example 3: Evaluation of Ability to Reduce Harmful Bacteria

The ability of the air-cleaning device according to Example 2 to reduce harmful bacteria such as *Aspergillus brasilliensis, Escherichia coli, Pseudomonas aeruginosa*, and *Staphylococcus aureus* subsp. *aureus* was evaluated by using a method according to KS I 2008:2013 of Korea Conformity Laboratories. That is, after a given concentration of test bacteria was dispersed in a chamber of 8 $m^3$ and the air-cleaning device was operated for 3 hours, a bacteria reduction rate in the chamber was measured, and the results are shown in Table 5 below.

TABLE 5

| No. | Test Bacteria | Bacteria reduction rate (%) |
|---|---|---|
| 1 | *Aspergillus brasilliensis*, ATCC 9642 | 93.4 |
| 2 | *Escherichia Coli.* ATCC 25922 | 99.9 |

TABLE 5-continued

| No. | Test Bacteria | Bacteria reduction rate (%) |
|---|---|---|
| 3 | *Pseudomonas aeruginosa*, ATCC 15442 | 99.9 |
| 4 | MRSA (*Staphylococcus aureus* subsp. *aureus*), ATCC 33591 | 99.9 |

Referring to Table 5, the air-cleaning device manufactured according to Example 2 exhibited a high ability to reduce harmful bacteria such as *Aspergillus brasilliensis, Escherichia coli, Pseudomonas aeruginosa*, and *Staphylococcus aureus* subsp. *aureus* with a bacteria reduction rate of 93.4% or more.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

The invention claimed is:

1. A catalyst structure for ozone decomposition, the catalyst structure comprising:
   a support comprising a porous inorganic material; and
   an $\alpha$-$MnO_2$ catalyst located on at least a portion of inner pores and a surface of the support, wherein the $\alpha$-$MnO_2$ comprises $\alpha$-$MnO_2$ particles with a diameter of about 50 nm to about 5 μm.

2. The catalyst structure of claim 1, wherein the porous inorganic material comprises a porous ceramic material.

3. The catalyst structure of claim 1, wherein the porous inorganic material comprises a porous ceramic material including 50% or more MgO, $SiO_2$, and $Al_2O_3$ components.

4. The catalyst structure of claim 3, wherein the porous ceramic material further comprises an alkali metal oxide.

5. The catalyst structure of claim 1, wherein the support is a monolith.

6. The catalyst structure of claim 1, wherein the support further comprises a material selected from glass, metal, plastic, or any combination thereof.

7. The catalyst structure of claim 1, wherein the $\alpha$-$MnO_2$ catalyst is fixed to the inner pores and the surface of the support in a binder-free state.

8. The catalyst structure of claim 1, wherein an amount of the $\alpha$-$MnO_2$ catalyst is in the range of about 1 part by weight to about 10 parts by weight based on 100 parts by weight of the support.

9. The catalyst structure of claim 1, wherein the catalyst structure for ozone decomposition further comprises a catalyst selected from $\beta$-$MnO_2$, $\gamma$-$MnO_2$, amorphous $MnO_2$, activated carbon, and any combination thereof.

10. A method of cleaning air, the method comprising:
    a first process of reducing hazardous gas including ethylene and harmful bacteria contained in the air using a photocatalyst reactor; and
    a second process of decomposing ozone generated in the first process by using the catalyst structure for ozone decomposition according to claim 1.

11. The method of claim 10, wherein the photocatalyst reactor comprises:
    a vacuum UV lamp; and
    one or more photocatalyst structures arranged around the vacuum UV lamp.

12. The method of claim 11, wherein the vacuum UV lamp comprises a UV-C lamp that emits light with wavelengths of 254 nm and 185 nm in a ratio of 9:1.

13. The method of claim 11, wherein the photocatalyst structure comprises:
    a substrate; and
    a $TiO_2$ photocatalyst arranged on the substrate.

14. The method of claim 10, wherein the hazardous gas comprises organic or inorganic hazardous gas comprising ethylene, ammonia, acetaldehyde, or any combination thereof.

15. The method of claim 10, wherein the harmful bacteria comprises *Aspergillus brasiffiensis, Escherichia coli, Pseudomonas aeruginosa, Staphylococcus aureus* subsp. *aureus*, or any combination thereof.

16. The method of claim 10, wherein the catalyst structure for ozone decomposition comprises at least one catalyst structure.

17. An air-cleaning device comprising: in a housing,
    a control area;
    an air inlet region;
    a first reaction chamber comprising a vacuum UV lamp and one or more photocatalyst structures arranged around the vacuum UV lamp;
    a second reaction chamber in which the catalyst structure for ozone decomposition according to claim 1 is located; and
    an air outlet region.

18. The air-cleaning device of claim 17, wherein air flows into or out of the air-cleaning device in one direction.

19. The air-cleaning device of claim 17, wherein a fan is installed in at least one of the air inlet region and the air outlet region.

20. The air-cleaning device of claim 17, wherein the catalyst structure for ozone decomposition comprises at least one catalyst structure.

21. An air-cleaning system comprising an air-cleaning device including the catalyst structure for ozone decomposition according to claim 1.

* * * * *